(12) United States Patent
Chang (10) Patent No.: US 6,454,739 B1
(45) Date of Patent: Sep. 24, 2002

(54) FIBRIN SEALANT DELIVERY DEVICE

(75) Inventor: Chong E. Chang, Kyonggi-Do (KR)

(73) Assignee: Korea Greencross Corp., Yongin-si (KR)

( * ) Notice: Subject to any disclaimer, the term of this patent is extended or adjusted under 35 U.S.C. 154(b) by 73 days.

(21) Appl. No.: 09/654,878

(22) Filed: Sep. 5, 2000

(30) Foreign Application Priority Data

Sep. 13, 1999 (KR) ........................ 1999-38999

(51) Int. Cl.[7] ..................... A61M 37/00; A61M 5/00; A61M 29/00; A61L 9/04; B05B 7/10
(52) U.S. Cl. ..................... 604/82; 604/191; 424/45; 239/399
(58) Field of Search ..................... 604/191, 82, 49, 604/89, 264, 912; 606/210, 192; 600/204; 239/399; 424/45

(56) References Cited

U.S. PATENT DOCUMENTS

| | | | |
|---|---|---|---|
| 3,767,085 A | * 10/1973 | Cannon et al. | 222/82 |
| 4,359,049 A | 11/1982 | Redl et al. | 128/218 |
| 4,655,747 A | * 4/1987 | Allen, Jr. | 604/89 |
| 4,735,616 A | 4/1988 | Eibl et al. | 604/191 |
| 4,813,928 A | * 3/1989 | Abe et al. | 604/49 |
| 4,874,368 A | * 10/1989 | Miller et al. | 604/82 |
| 4,978,336 A | 12/1990 | Capozzi et al. | 604/82 |
| 4,979,942 A | 12/1990 | Wolf et al. | 604/83 |
| 5,104,375 A | 4/1992 | Wolf et al. | 604/56 |
| 5,116,315 A | * 5/1992 | Capozzi et al. | 604/82 |
| 5,174,653 A | 12/1992 | Halat et al. | 366/339 |
| 5,368,563 A | 11/1994 | Lonneman et al. | 604/82 |
| 5,474,540 A | * 12/1995 | Miller et al. | 604/191 |
| 5,582,595 A | 12/1996 | Haber et al. | 604/187 |
| 5,665,067 A | 9/1997 | Linder et al. | 604/82 |
| 5,759,167 A | 6/1998 | Shields, Jr. et al. | 602/26 |
| 5,759,171 A | 6/1998 | Coelho et al. | 602/82 |
| 5,861,002 A | * 1/1999 | Desai | 606/210 |
| 5,887,755 A | 3/1999 | Hood, III | 222/135 |
| 6,120,437 A | * 9/2000 | Yoon et al. | 600/201 |
| 6,146,401 A | * 11/2000 | Yoon et al. | 604/164.01 |

* cited by examiner

Primary Examiner—Anhtuan T. Nguyen
Assistant Examiner—Roz Ghafoorian
(74) Attorney, Agent, or Firm—Staas & Halsey LLP (57) ABSTRACT

An improved delivery device for applying two-component adhesives such as fibrin sealant is disclosed. The improved delivery device includes a pair of syringe bodies for storing a first and a second adhesive components, respectively, a pair of plungers associated with the pair of syringe bodies for expelling the first and the second component from the pair of syringe bodies, and a pair of needles. The needles are connected to the syringe bodies for providing separate passages for the components, and have distal end surfaces which are apart from each other with a predetermined distance, and faced each other with an angle in the range of 10° to less than 180°.

8 Claims, 8 Drawing Sheets

Prior Art

Fig. 3

Prior Art

Fig. 4

Prior Art

FIBRIN SEALANT DELIVERY DEVICE

BACKGROUND OF THE INVENTION

1. Field of the Invention

The present invention relates to the design of an improved delivery device for applying two-component adhesives such as fibrin sealant. More particularly, the delivery device includes needles for separately ejecting two adhesive components (such as fibrinogen and thrombin) so that the ejected components are impinged and mixed, and thereby clotted to seal a wound, stop bleeding or the like.

2. Description of the Related Art

Blood is coagulated through several steps of chain reactions between various proteins in blood. The final stage of the coagulation cascade can be depicted as the following biochemical reactions between fibrinogen, factor XIII, and thrombin.

As shown in the above reactions, fibrinogen is proteolytically cleaved into fibrin monomer by thrombin, and factor XIII, which is a calcium dependent enzyme, is proteolytically cleaved by thrombin in the presence of calcium ion into an activated form (Factor XIIIa). The activated factor XIII converts the noncovalently assembled fibrin monomer into cross-linked and covalently bonded fibrin fiber having a three-dimensional network.

Fibrin sealant (also called fibrin glue or fibrin adhesive), which is a representative example of the two-component biological sealant, exploits the final stage of the coagulation cascade. The main ingredient of the first component includes fibrinogen and factor XIII, and the main ingredient of the second component includes thrombin and calcium chloride that works as a catalyst for the coagulation reaction. By mixing the two components just prior to use, and applying the mixed components on a wound of a patient, the two components undergo a rapid coagulation to seal the wound.

Figure 1A:
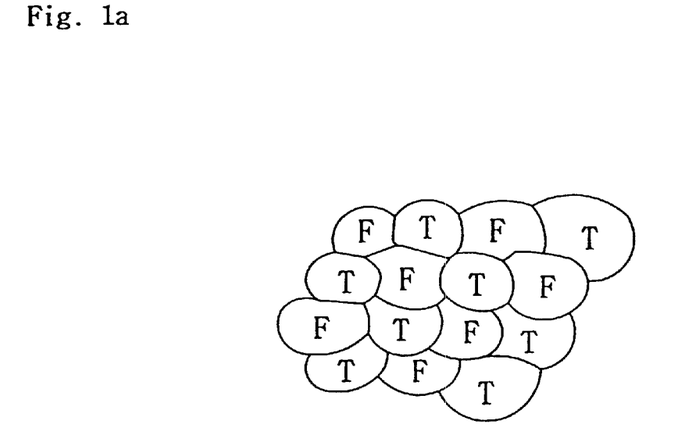
FIG. 1a is a drawing for illustrating the mixed state of the first component including fibrinogen and the second component including thrombin.
Figure 1B:
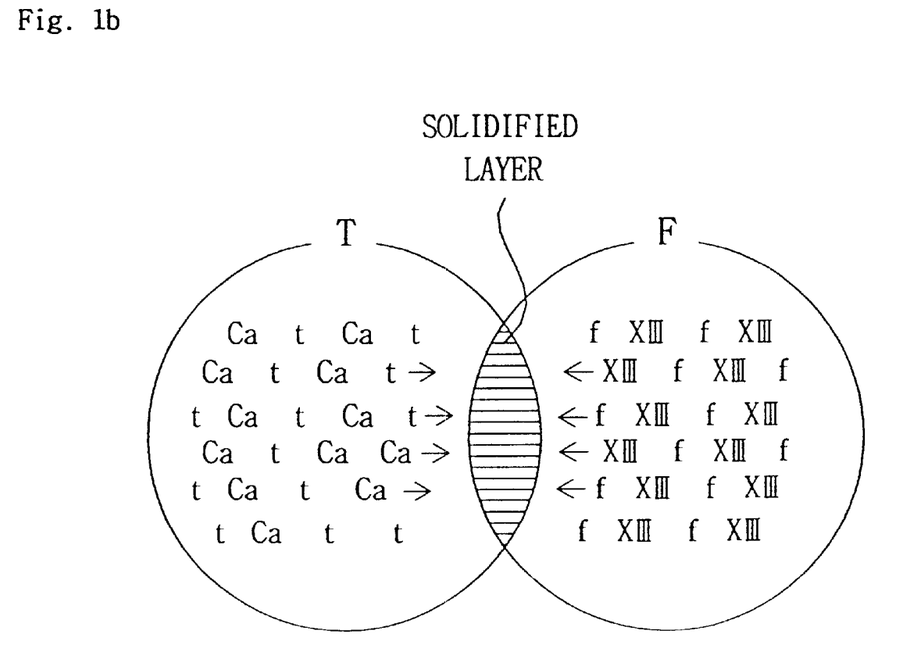
FIG. 1b is a schematic diagram for illustrating the coagulating process of fibrinogen and thrombin

FIG. 1a is a drawing for illustrating the mixed state of the first component including fibrinogen and the second component including thrombin, and F and T in FIG. 1a denote heterogeneous components including fibrinogen and thrombin, respectively. As shown in FIG. 1a, the fibrin glue coagulation process is a heterogeneous reaction between layers or drops of the two components F and T, thus the coagulation reaction is carried out on the surfaces of the layers or drops of the components. FIG. 1b is a schematic diagram for illustrating the coagulating process of fibrinogen and thrombin. In FIG. 1b, f, t, XIII and Ca denote fibrinogen, thrombin, factor XIII and calcium ion, respectively. As shown in FIG. 1b, the first coagulation layer is formed on the boundary of the layers or drops of the two components T and F, and the unreacted components would be trapped in pockets between these initially solidified layers. Further coagulation continues only by the diffusion of the fibrinogen f or thrombin t through the solidified layer formed on their boundary. Since the boundary prevents the diffusion of the thrombin and/or fibrinogen, and the diffusion coefficients of the proteins is generally low compared to organic or inorganic molecules, the further coagulation is retarded due to the gel-type solidified layer formed on the boundary. Thus, the high degree of mixing of the two components is important for applying the fibrin sealant to seal a wound, stop bleeding or the like. In addition, the two components should be preserved separately prior to be applied to a patient for preventing coagulation of the two components before use or in delivery device.

Various types of delivery devices for applying the two components fibrin sealant to a patient are disclosed in prior arts. For example, delivery devices using a pressurized gas to eject the sealant components are disclosed in U.S. Pat. Nos. 5,582,595, 5,665,067, 5,759,167 and 5,887,755. The delivery devices have problems in that intricate parts have to be used to precisely control the pressure of the ejected components, a sanitized gas supplying system is required, and the components are sprayed to the target area only in aerosol form.

Figure 2:
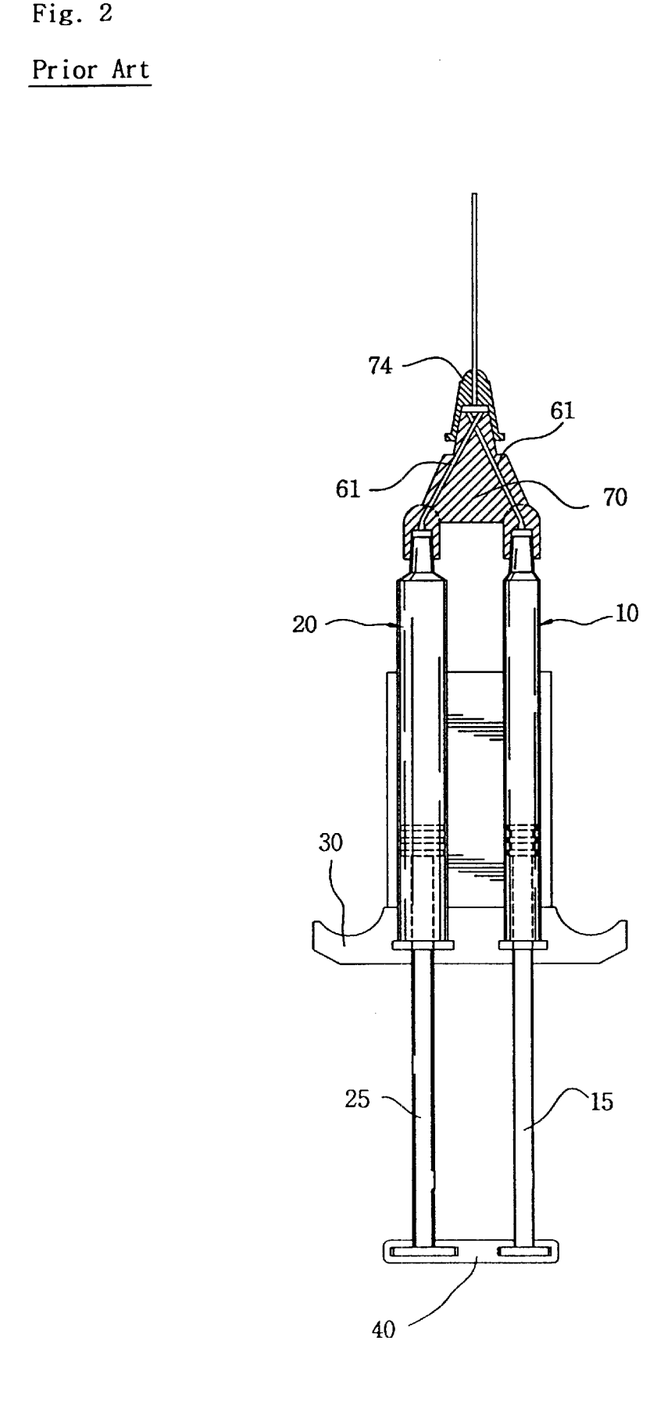
FIG. 2 is a plan view of the prior fibrin sealant delivery device having internal mixing part.

There are other types of the delivery system having internal mixing parts such as mixing needle, cell, well, or syringe tube (U.S. Pat. Nos. 4,359,049, 4,978,336, 4,735,616, 4,979,942, 5,104,375 and 5,116,315, 5,174,653). An exemplary device of this kind is disclosed in U.S. Pat. No. 4,735,616, and is shown in FIG. 2. As shown in FIG. 2, the fibrin sealant delivery system includes a pair of syringe body 10 and 20 supported by a connecting member 30, and piston type plungers 15 and 25 are provided for actuating the components from the syringe bodies 10 and 20. The upper ends of the piston type plunger 15 and 25 are connected by a connecting clip member 40 for simultaneously pressing the plungers 15 and 25. The delivery system includes a connecting head 70 which is attachable to the bodies 10 and 20, and includes conveying channels 61. A mixing needle 74 is attached to the other end of the connecting head 70. The conveying channels 61 are spirally twisted to enhance the mixing efficiency of the two components in the mixing needle 74, and the components mixed in the mixing needle 74 are ejected and applied to a treatment site.

However, in this device, the volume of the mixing needle 74 is generally small, and the retention time of the components in the mixing needle 74 is not enough for the sufficient mixing of the components. The mixing efficiency of the delivery systems can be improved if the flow rate for inducing turbulence of the components becomes higher. However, if the flow rate gets higher, there is possibility of forming undesirable bubbles during the flow of fluid in the device. Other drawback of the device is the clotting of the device due to the coagulation of the two components in the mixing needle. If the flow of the sealant is temporarily stopped during surgery, the clotting of device is more liable to happen.

Figure 3:
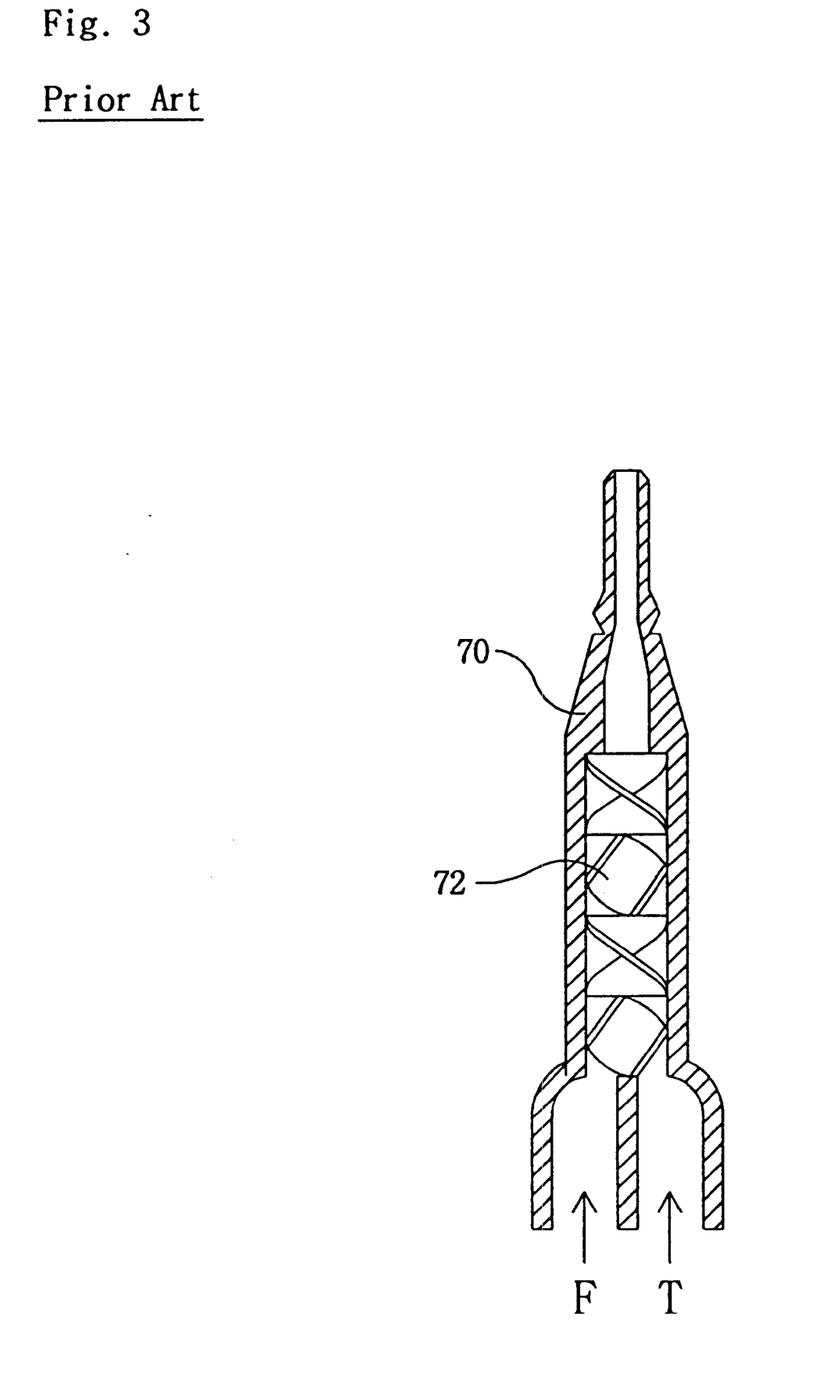
FIG. 3 is a cross sectional view of the internal mixing part of other prior fibrin sealant delivery device.

U.S. Pat No. 5,174,653 discloses the delivery device having a connecting head containing a spirally molded element to produce turbulences in the stream of the conveyed components. FIG. 3 is a cross sectional plan view of the connecting head containing the spirally molded element. As shown in FIG. 3, the two components T and F which are in-flowed into the connecting head 70 are completely mixed due to the turbulence produced by the spirally molded elements 72. However, the two components in the connecting head 70 are easily coagulated and clots the connecting head 70 which prevent further use of the device. In addition, due to the complex configuration of the spirally molded element 72, it is difficult and expensive to produce the device.

To overcome the drawbacks, U.S. Pat. Nos. 4,874,368, 5,474,540, 5,368,563 and 5,759,171 disclose delivery devices for conveying and ejecting the two components through separate passages. U.S. Pat. No 4,874,368 disclose delivery devices having two parallel syringe tubes and needles for containing and ejecting each component. U.S. Pat. Nos. 5,368,563, 5,474,540, and 5,759,171 disclose delivery devices having means for ejecting the components in a swirling pattern for sufficient mixing of the components. However, the means generally have complex channels which have to be drilled, molded or otherwise formed, thus it is difficult and expensive to produce the swirling means due to its complex structure.

Figure 4:
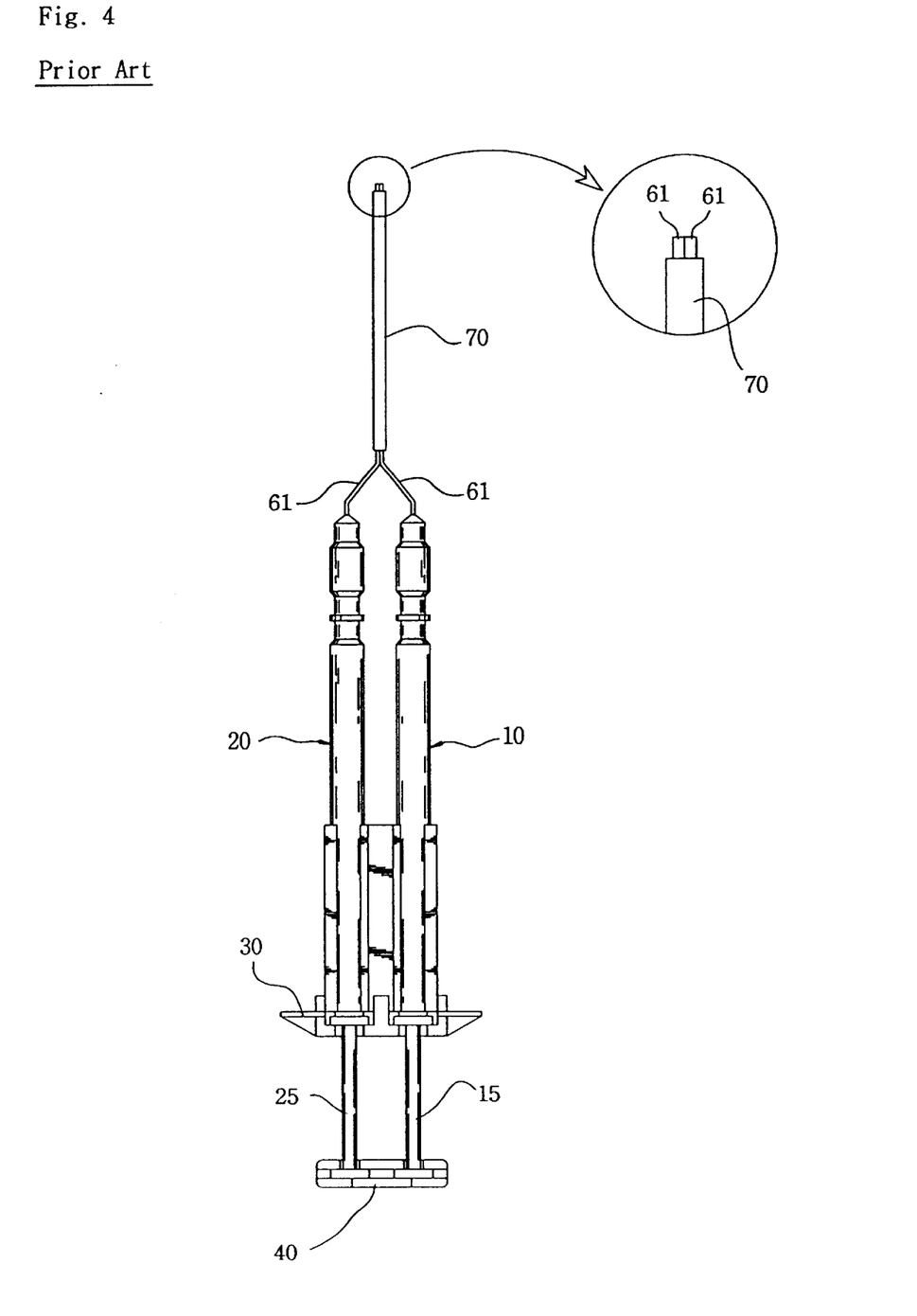
FIG. 4 is a plan view of a prior fibrin sealant delivery device having parallel needle ends.

The fibrin sealant delivery system of U.S. Pat. No. 4,874, 368 is shown in FIG. 4. As shown in FIG. 4, The fibrin sealant delivery system includes a pair of syringe body 10 and 20, a connecting member 30, piston type plungers 15 and 25, and a connecting clip member 40 which have the same functions with the corresponding members in FIG. 2. In FIG. 4, reference numeral 70 is a hollow sleeve for holding the needles 61 together. As shown in FIG. 4, the delivery system includes the separate syringe bodies 10 and 20, and needles 61 for separately delivering the two components to the target site. Thus, the fibrin glue sealant cannot be mixed in the system, and the clotting of the syringes 10 and 20 or needles 61 can be partly prevented. However, in this case, since the end portions of the needles 61 are adjacent to each other, it is possible for one component ejected from a needle 61 can be attached to the end of the other needle 61. Thus, when the delivery devices is not in use in surgery, the clogging would happen at the ends of the needles 61, which prevent further use of the delivery device. In addition, since the two needles 61 are in parallel, the mixing of the two ejected components is insufficient, and the coagulation of the two components on a treatment site is possibly incomplete.

SUMMARY OF THE INVENTION

It is accordingly an object of the present invention to provide a new two-component sealant delivery device which permits rapid and complete blending of the two components.

It is another object of the present invention to provide a two-component sealant delivery device which prevents clogging of the needles or syringes of the device.

It is yet another object of the present invention to provide a sealant delivery device which has simple structure and is produced with low cost.

A further object of the present invention is to provide a two-component sealant delivery device for blending and mixing the two components outside of the device and enlarging the application area of the mixed two components.

To accomplish these and other advantages, the present invention provides a delivery device for applying two-component adhesives to a treatment site, which includes a pair of syringe bodies for storing a first and a second adhesive components, respectively, a pair of plungers associated with the pair of syringe bodies for expelling the first and the second component from the pair of syringe bodies; and a pair of needles connected to the syringe bodies for providing separate passages for the components. The pair of needles have distal end surfaces which are apart from each other with a predetermined distance, and faced each other with an angle in the range of 10° to less than 180°.

The present invention also provides a delivery device for applying two-component adhesives to a treatment site including a pair of needles having needle ends for ejecting the components so that the ejected component are impinged and redirected to the treatment site.

The present invention further provides a delivery device for applying two-component adhesives to a treatment site including a pair of needles connected to the syringe bodies for providing separate passages for the components, wherein the needles includes needle bodies which are connected to the syringes and bent to be held together, and needle ends which extends from the needle bodies, and bent outwardly and then inwardly along with the direction of ejected components to apart the distal end surfaces of the needle ends.

DETAILED DESCRIPTION OF THE PREFERRED EMBODIMENT

For a better understanding of the present invention, reference will now be made in detail to the following disclosures and appended drawings.

Figure 5:
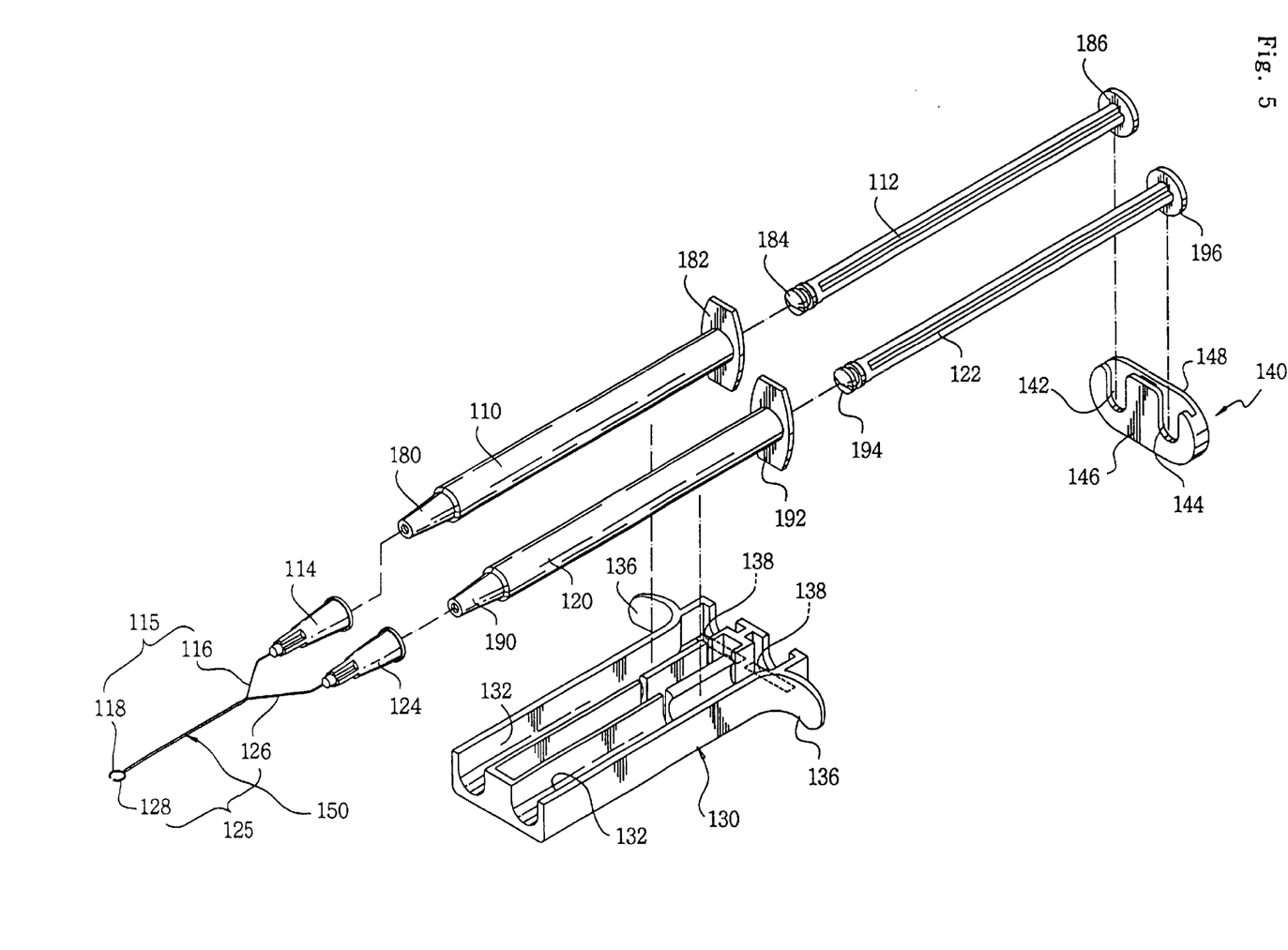
FIG. 5 is an exploded perspective view of the two-component sealant delivery device according to a preferred embodiment of the present invention.
Figure 6:
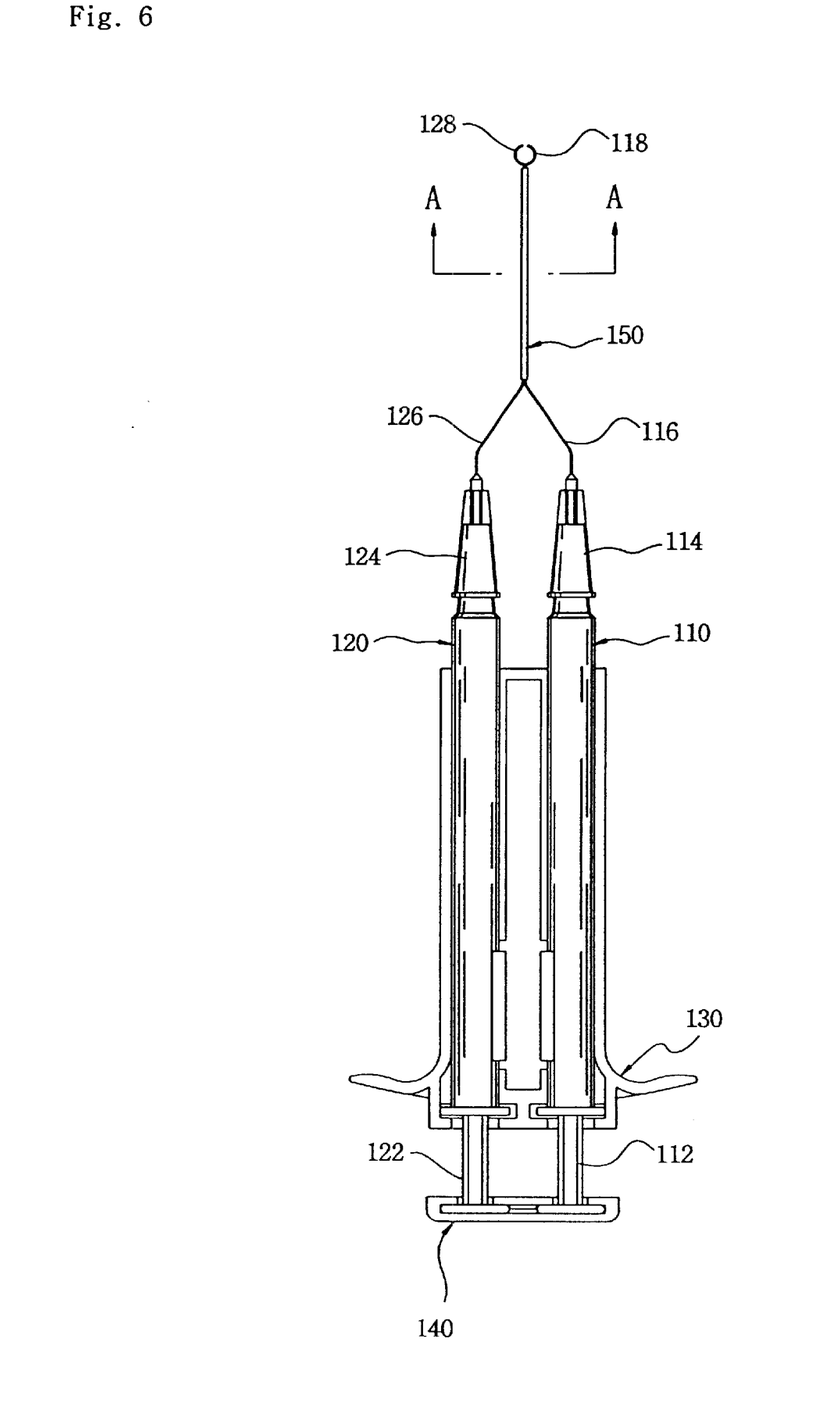
FIG. 6 is a plan view of the two-component sealant delivery device according to a preferred embodiment of the present invention.

FIGS. 5 and 6 are an exploded perspective view and plan view of the sealant delivery device according to the preferred embodiment of the present invention, respectively. As shown in FIG. 5, the device of the preferred embodiment includes a pair of syringe bodies 110 and 120 which are held together by a syringe holder 130. Each syringe body 110 and 120 is a typical and standard syringe tube available from many manufacturers, and preferably includes tapered portion 180 and 190 at one end, and flanges 182 and 192 at the other end for securing the syringe body 110 and 120 to user's finger or other element. In operation, two components of the sealant, for example, fibrinogen and thrombin solutions, are filled in the pair of syringe bodies 110 and 120, respectively. The diameters of the syringe bodies 110 and 120 can be equal or different according to the type of the sealant in use.

Associated with each of the syringe bodies 110 and 120 are piston type plungers 112 and 122 for pressing and expelling the loaded components in the syringe bodies 110 and 120. The piston type plungers 112 and 122 are also typical and standard members used with the standard syringe tubes 110 and 120, and preferably include fitting ends 184 and 194 which tightly fits with the internal shapes of the syringe bodies 110 and 120, and push flanges 186 and 196 at the other ends for easily pressing the piston type plungers 112 and 122 to the direction of the needles 116 and 126.

Figure 8:
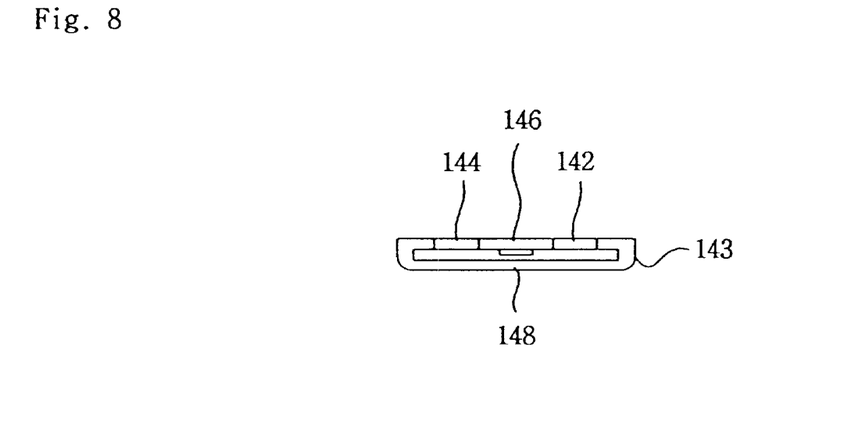
FIG. 8 is a cross-sectional view of the connecting member of the two-component sealant delivery device according to a preferred embodiment of the present invention.

The piston type plungers 112 and 122 are secured to a connecting member 140 so that the two piston type plungers 112 and 122 can be actuated simultaneously by pressing the connecting member 140. In the preferred embodiment, the connecting member 140 is designed to catch the push flanges 186 and 196. The connecting member 140 includes a top member 148, a base member 146 and at least on side member 143 for maintaining the top and base members 148 and 146 in parallel (See FIG. 8). Two slots 142 and 144 are formed at the base member 146, and the sizes of the two slots 142 and 144 are smaller than the diameters of push flanges 186 and 196, and larger than the diameters of the piston type plungers 112 and 122 for securing and catching the push flanges 186 and 196 between the top member 148 and the base member 146.

Figure 7:
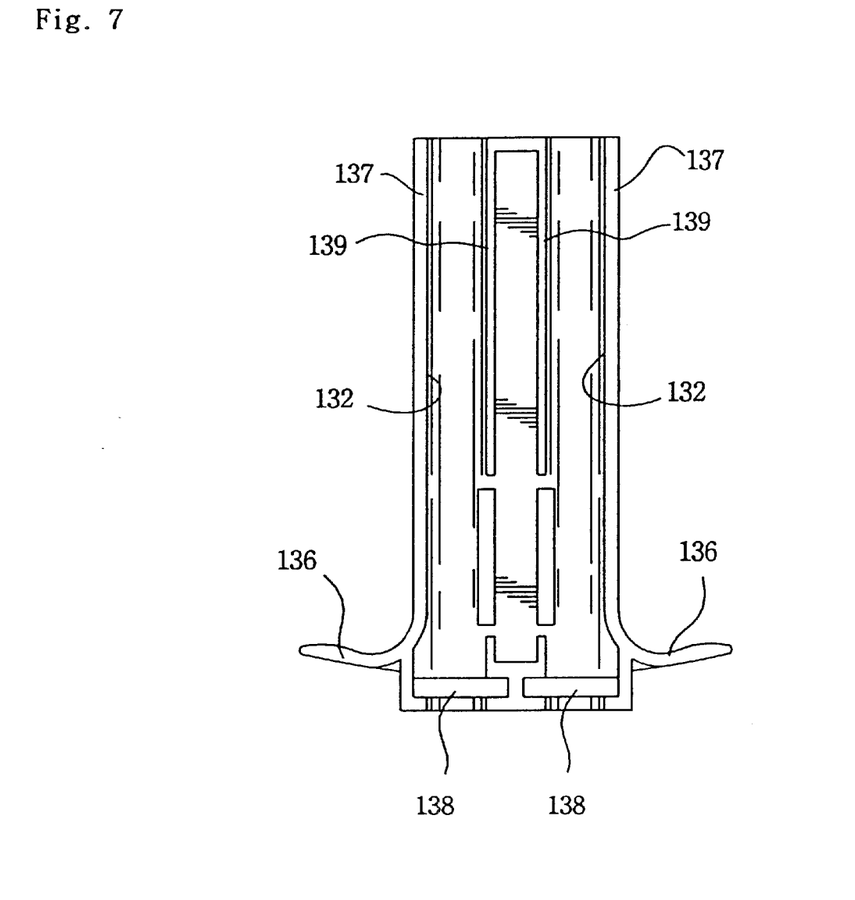
FIG. 7 is a plan view of the syringe holder of the two-component sealant delivery device according to a preferred embodiment of the present invention.

Referring to FIGS. 6 and 7, the syringe holder 130, generally made of a molded plastic, has two open faced semi-cylindrical channels 132 for tightly receiving the syringe bodies 110 and 120, respectively, and two slots 138 are formed at the end of each channels 132 for receiving the flanges 182 and 192 of the syringe bodies 110 and 120 to prevent the movement of the bodies 110 and 120 along with the cylindrical channels 132. Preferably, two flange members 136 are projected from the outer walls 137 of the semi-cylindrical channels 132 for fixing user's fingers. For securely retaining the received syringe bodies 110 and 120, at least one of the walls 137 and 139 of the semi-cylindrical channels 132 is partially or fully tapered to have a slightly smaller diameter at the upper ends of the semi-cylindrical channels 132.

In this preferred embodiment, even though the syringe holder 130 is used for receiving and securing the syringe bodes 110 and 120, various means, such as adhesive, can be used for securing the syringe bodes 110 and 120 together instead of the syringe holder 130.

Referring to FIGS. 5 and 6, two connectors 114 and 124 are preferably secured to the tapered portions 180 and 190 of the syringe bodies 110 and 120 to attach a pair of needles 115 and 125 to the ends of the syringe bodies 110 and 120. In some case, the needles 115 and 125 can be directly attached to the syringe bodies 110 and 120 without using the connectors 114 and 124. As shown in FIGS. 5 and 6, in a preferred embodiment of the present invention, needles 115 and 125 includes needle bodies 116 and 126 which are bent to be held together by a needle sleeve 150, and needle ends 118 and 128. The needle sleeve 150 receives each of the needle bodies 116 and 126 to hold the needle bodies 116 and 126 together in the desired relationship.

Figure 9A:
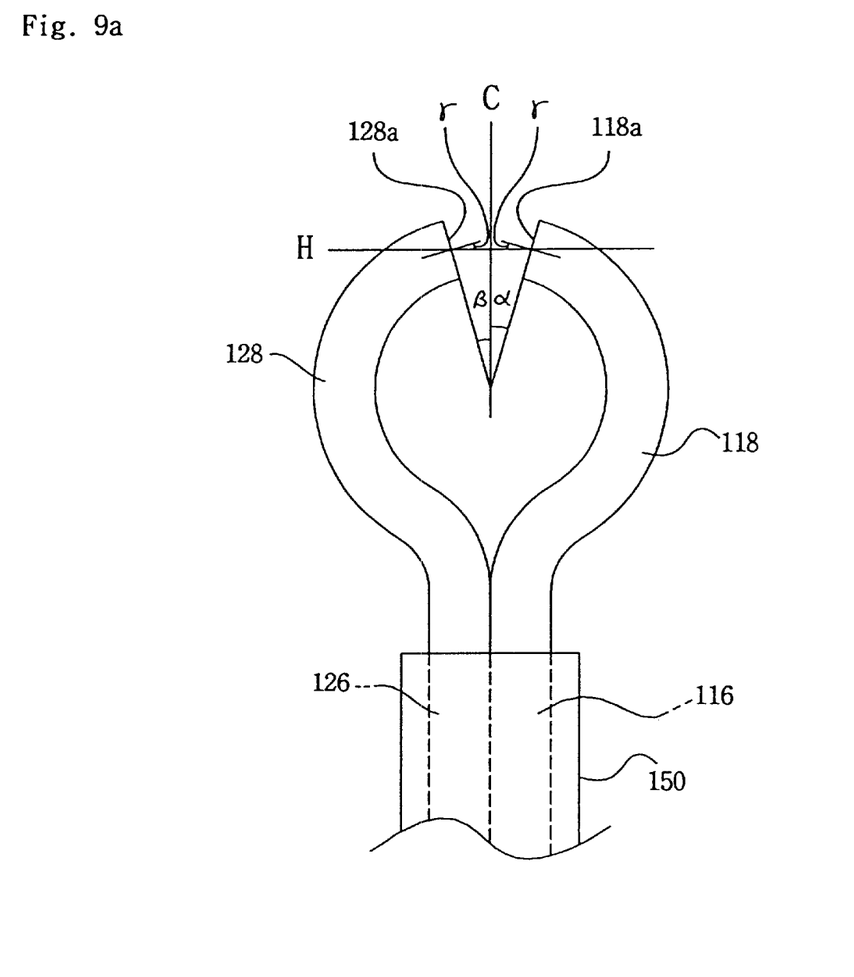
FIG. 9a is an enlarged view of the needle ends of the two-component sealant delivery device according to a preferred embodiment of the present invention.

FIG. 9a is an enlarged view of the needle ends 118 and 128 of the two-component sealant delivery device according to a preferred embodiment of the present invention. As clearly shown in FIG. 9a, in one preferred embodiment of the present invention, the needle ends 118 and 128, which extends from the needle bodies 116 and 126, are bent outwardly at the end portions of the needles 115 and 125, and then bent inwardly as they go to the distal ends of the needles 115 and 125 so that the distal end surfaces 118a and 128a are faced each other and apart from each other.

Preferably, the needles ends 118 and 128 are configured to eject the components so that the ejected component are impinged and redirected to the treatment site. More preferably, the needles ends 118 and 128 are bent to have the shape of partially opened circle which has open portion on the symmetry axis C of the needle bodies 116 and 126.

In one aspect of the present invention, the distal end surfaces 118a and 128a are faced with each other, and separated or apart from each other with a predetermined distance. The sum of the angles ($\alpha$, $\beta$) between the distal end surfaces 118a and 128a and an axis of symmetry C of the two needles 116 and 126, in short, the angle between the distal end surfaces 118a and 128a is in the range of $10°<\alpha+\beta<180°$, and preferably in the range of $30°<\alpha+\beta<120°$.

In the other aspect of the present invention, the needle ends 118 and 128 are bent so that the angle($\gamma$) between the horizontal line H and the direction of ejected stream of component is in the range of $5°<\gamma<90°$, and preferably in the range of $15°<\gamma<60°$ (See FIG. 9a).

Figure 9B:
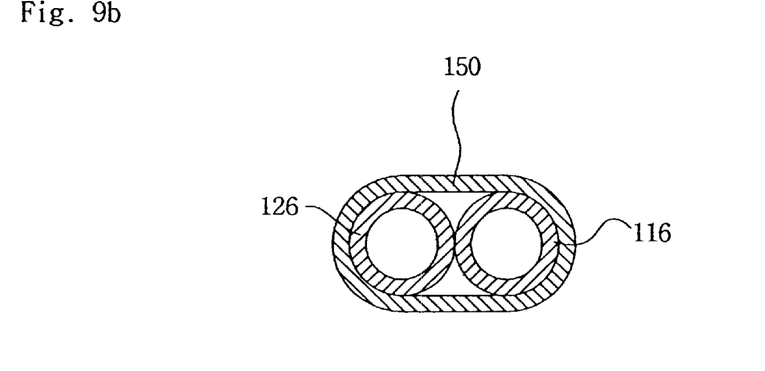
FIG. 9b is a cross-sectional view through Line A—A of the delivery device in FIG. 6.

FIG. 9b is a cross section view through Line A—A of the delivery device in FIG. 6. As shown in FIG. 9b, the needle sleeve 150 preferably holds together the two needle bodies 116 and 126.

In operation, two sealant components are loaded into the syringe bodies 110 and 120, and while directing the needle ends 118 and 128 to a treatment site, the connecting member 140 is pressed to actuate the piston type plungers 112 and 122. The two components in the syringe bodies 110 and 120 pass through the needles 115 and 125, and ejected from the distal end surfaces 118a and 128a of the needle ends 118 and 128, respectively. Since the distal end surfaces 118a and 128a are designed to be faced each other with predetermined angle, the two components which are ejected from the distal end surface 118a and 128a, respectively, are severely impinged around the axis of symmetry C, and redirected along the symmetry axis C to the treatment site. The two ejected components are sufficiently mixed in the process, and coagulated immediately after they reach the treatment site.

In this mixing process, the bubble formation in the coagulated clots, which is one of the major drawback in the system using internal mixing process, could be prevented. In addition, since the distal ends are separated from each other with a predetermined distance and angle, the component ejected from a distal end surface could not reach the other needle end, thus the coagulation of the two components at the needle ends and clogging of needles can be prevented. Furthermore, because the two components are maintained separately in the syringe and conveyed along the completely different passage, the clogging of syringe can be prevented even when the ejection of the components from the syringe is temporarily stopped.

The distance between the distal end surfaces can be determined according to the diameter of needle and to provide sufficient contact area of the two components before they reach the treatment site. The width of spray of the mixed components can be controlled by changing the angle between the distal end surfaces. When the angle between the distal end surfaces is larger, the spray of the mixed component covers smaller area of the treatment site. In contrast, when the angle between the distal ends is smaller, the spray of the mixed component covers larger area of the treatment site. As stated above, the preferable angle between the distal end surfaces is in the range of 10° to less than 180°, and more preferably 30° to less than 120°.

In order to more fully illustrate the preferred embodiments of the present invention and to elucidate the relationship of mixing with the clotting rate of fibrin sealant, four different devices, (1) the impinging dual syringe device according to a preferred embodiment of the present invention, (2) dual syringe having adjoined needle ends, which is same type with that disclosed in FIG. 4 and U.S. Pat. No 4,874,368, (3) endoscopic delivery device, which is same type with that disclosed in FIG. 2 and U.S. Pat. No. 4,735,616, and (4) static spiral mixing element device, which is same type with that disclosed in FIG. 3 and U.S. Pat. No. 5,174,653 are evaluated as follows.

Preparation of Materials

Standard Fibrin Glue

Component A contains 80 mg/ml fibrinogen, 0.8 mg/ml fibronectin, 17.2 mg/ml albumin, 75 IU/ml factor XIII and 1213 kallikrein inhibiting unit(KIU)/ml aprotinin. It is prepared by dissolving Greenplast(Korea Green Cross Corp, Korea) vial 1 containing the freeze-dried fibrinogen with solution in vial 2 containing aprotinin.

Component B contains 600 IU/ml human thrombin and 5.6 mg/ml calcium chloride. It was prepared by dissolving Greenplast(Korea Green Cross Corp) vial 3 containing freeze-dried human thrombin with solution in vial 4 containing calcium chloride.

Diluted or Concentrated Fibrin Glue

Diluted or concentrated fibrinogen solution for component A is prepared by dissolving the vial 1 with 2 ml or 0.7 ml of vial 2 respectively, resulting in 40 mg/ml or 114 mg/ml fibrinogen. Also diluted or concentrated thrombin solution for component B is prepared by dissolving the vial 3 with 3 ml or 0.6 ml of vial 4 respectively, resulting in 200 IU/ml or 1000 IU/ml thrombin.

Application Device

1) Impinging dual syringe device

The syringe devices used for this experiment are made of 22 gauge or 25 gauge 316 stainless steel needles having an impingement angle(180°-2γ) of 30°. (See FIG. 9a) The length is 1.5 inches for 25 gauge needles and 2 inches for the 22 gauge needles.

The exit ends of the needle are bent around so that the open ends of needles are directly faced each other (See FIG. 9a). The angle formed by the needles at the exit ends will be impingement angle of the jet streams of component A and component B. As the two jet streams impact and collide, two components are intimately and freely mixed without any drag effect on the stream. As the exit positions of two tubes are apart far enough, there is no danger of clogging the device even if delivery of the fibrin glue is stopped during application.

2) Dual syringe having adjoined needle ends

Two 25 gauge 316 stainless steel needles of 0.012 inch ID are assembled in parallel as shown in FIG. 4. The length is 1.5 inches and the exit point is joined at the same position as shown in FIG. 4. Component A and component B passes through the Y-shaped needles to a treatment site.

3) Endoscopic delivery device

The syringe includes a mixing needle 74 having 22 gauge 316 stainless steel needle of 0.02 inch ID and 1.25 inch long (See FIG. 2). Upper end of the mixing needle 74 is attached to Y-shaped plastic dual lumens(connecting head 70) which is connected to dual syringe bodies. Component A and component B contained in syringe bodies are delivered simultaneously by the piston pumps. The two fibrin glue components mix passively in the mixing needle 74 while exiting the needle.

4) Static Spiral Mixing Element Device

This device (Tah Industries, Inc. U.S.A., part no 190-212PE) includes a series of left and right handed helical elements in the connecting head 70 as shown in FIG. 3. The connecting head used for our experiment is 1.5 inch long and 0.093 inch in OD and contains twelve spirally molded mixing elements. The entering fluids are progressively divided and recombined, forming striated layers. This is expected to be one of the most efficient mixing device, particularly for a viscous fluid such as fibrinogen solution.

Test Methods

Viscosity Measurement

Viscosity of component A (9.0% fibrinogen) and component B (600 IU/mi thrombin) is measured by using Brookfield Viscometer (Model No DV-II+, Brookfield Engineering Labs Inc, U.S.A.). The measured viscosity at 25° C. is 29.4 centipoises for Component A and 1.0 centipoises for component B. The viscosity of 75% Glycerol by weight is equivalent to that of 9.0% fibrinogen solution and used for the color simulation experiments.

Color Visualization for Mixing

A: Simulation Experiment

Viscosity is the most critical parameter in determining the mixing efficiency of a liquid. Simulated color visualization experiment is performed by using 75% Glycerol solution and 0.125% Brilliant Blue R dye solution (C.I. 42660 Coomassie, Sigma Chemical Co. U.S.A.). Four different application devices as described above are used. The delivery speed is controlled by using Dilutrend (Type B1, Boehringer Mannheim GmbH, Switzerland). 0.25 ml of each solution is simultaneously delivered on glass plate at a rate of 1 ml per 9 seconds (or 2.25 seconds/0.25 ml) from 1 cm above the plate.

B: Fibrin Glue Experiment:

0.25 ml of 9% fibrinogen solution and 0.25ml of 600 IU/ml thrombin solution with 0.125 % Brilliant Blue R dye are delivered simultaneously at a rate of 1 ml per 9 seconds by the same manner as described above.

C: Clotting Rate Measurement

Component A and component B are loaded separately into the syringe bodies up to the volume of 0.25 ml each. The delivery unit is vertically mounted on Dilutrend. The dispensing speed is programmed to adjust 2 through 9 seconds per stroke. The fibrin glue exit point is faced downward and the fibrin glue is delivered vertically to the glass plate located one centimeter away under the exit point. The glass plate is inclined 30 degrees and the delivered fibrin glue freely flows down until it sets up. The distance from injection point to the end point of flow is measured and is termed 'Flow Distance' as an indirect measure of clotting rate.

Results

A: Color Visualization

75% Glycerol is a clear liquid. Its viscosity was same as that of 9% fibrinogen solution. 0.125% Brilliant Blue R dye solution is a blue colored liquid having a viscosity of 1.0 centipoises similar to the thrombin solution. When these two simulated liquids were simultaneously delivered on glass plate by using different devices as mentioned earlier, the degree of mixing could be visualized by the streaks of clear and blue colored layers. However, the color streaks disappeared within a few minutes and became uniform solid blue color. This indicates that incompletely mixed mixture of the two liquids became homogeneous due to the diffusion process. When the color was observed at the instant of mixing for different type of devices, it revealed a different degree of mixing depending on devices in the following order of efficiency 1. Static spiral mixing element device 2. Impinging dual syringe device 3. Single tube endoscopic delivery device and 4. Dual syringe having adjoined needle ends. When the static spiral mixing element device was used, no color streak was recognized even at the instant of injection, and it was found to be the most efficient mixing device among the tested devices in this experiment.

B: Color Visualization using fibrin glue

When fibrin glue is used for the color visualization experiments, a remarkable difference was found in that the blue color streaks appeared initially stayed in the same pattern as a result of solidification of the fibrin glue. Only a slight smearing of color was observed after an hour. When the static spiral mixing element device was used for the standard fibrin glue, the device was clogged after ejaculating only one or couple of drops. The drops were clotted instantly. The measured volume in the mixing element is 0.06 ml and the estimated retention time is only a half second. Very fast setting must have been occurred on the way of passing through the element as a result of intimate mixing by a repeated splitting and formation of fine layers of mixed components as mentioned earlier.

C: Clotting Rate Depending on Application Device

Clotting rate was observed for four different application devices by using the same fibrin glue for all experiments containing 80 mg/ml fibrinogen in component A and 600 IU/ml thrombin in component B. A volume of 0.25 ml for each component was delivered at a rated speed of one ml per 9 seconds. Three separate tests were performed for each device and the resultant flow distance was measured (table. 1). The average flow distance was longest (slowest clotting) when dual syringe having adjoined needle ends was used, and the flow distance was shorter in the following order; single tube endoscopic delivery device, impinging dual syringe device (22 Ga), impinging dual syringe device (25Ga), and static spiral mixing element device. As expected from the result of color visualization test, fibrin glue delivered by the static spiral mixing element device was instantly set and no flowing was observed (table.1).

TABLE 1

Clotting Rate of Fibrin Glue for Different Application Devices.

| Application Device | Flow Distance (cm) | Average Flow Distance (cm) |
|---|---|---|
| dual syringe having adjoined needle ends | 4.5<br>5.5<br>5.7 | 5.2 |
| single tube endoscopic delivery device | 3.6<br>3.0<br>2.8 | 3.1 |
| Impinging dual syringe device (22Ga) | 2.6<br>1.5<br>2.4 | 2.2 |
| Impinging dual syringe device (25Ga) | 1.3<br>2.0<br>1.5 | 1.6 |
| static spiral mixing element device | 0.0<br>0.0<br>0.0 | 0.0 |

D: Clotting Rate Depending on Fibrinogen and Thrombin Concentrations.

The fibrinogen concentration in component A varied 40, 80, and 114 mg/ml and the thrombin in component B was 200, 600, and 1000 IU/ml. The clotting rate for each sample was measured by using 0.25 ml of each component, and they were simultaneously delivered by using dual syringe having adjoined needle end at a speed of 0.25 ml per 2.25 seconds (table.2). The same test was performed in the same manner by using the impinging dual syringe device (22Ga) (table.3).

In general, the flow distance got longer as the fibrinogen concentration decreased and as the thrombin concentration decreased. But the variations of the thrombin concentration seemed to play a greater role on clotting rate. The mixing of the two components appeared to be more efficient with the impinging dual syringe device than the dual syringe having adjoined needle end as indicated by the faster setting of the applied fibrin glue. Moreover, the effect of concentration of the fibrinogen and the thrombin on the clotting rate appeared to be less pronounced when the efficiency of mixing was improved.

TABLE 2

Clotting Rate Depending on Various Fibrinogen and Thrombin Concentrations by Using Dual Syringe having adjoined needle ends.

| Fibrinogen Conc, | Clotting Rate by Flow Distance, cm Thrombin Conc, IU/ml | | |
|---|---|---|---|
| mg/ml | 200 | 600 | 1000 |
| 40 | 11.0 | 6.0 | 2.8 |
| 80 | 7.0 | 4.5 | 2.0 |
| 114 | 4.0 | 2.0 | 1.5 |

TABLE 3

Clotting Rate Depending on Various Fibrinogen and Thrombin Concentrations by Using Impinging Dual Syringe Device (22Ga).

| Fibrinogen Conc, | Clotting Rate by Flow Distance, cm Thrombin Conc, IU/ml | | |
|---|---|---|---|
| mg/ml | 200 | 600 | 1000 |
| 40 | 4.0 | 2.4 | 0.9 |
| 114 | 3.2 | 1.5 | 0.0 |

E: Effect of Application Speed

Clotting rate was evaluated for both 22Ga and 25Ga size impinging dual syringe devices by using 0.25 ml of standard components A and B (table. 4). Component A Contains 80 mg/ml Fibrinogen and Component B 600 IU/ml thrombin. Delivery speed was adjusted at a rate of 1 ml per 2, 4, 6, or 9 seconds by using the Dilutrend dispensing machine. In general, the flow distance was shorter as the application speed was lowered for both devices. However, the clotting rate was faster when 25Ga device was used. This may be caused by a more efficient mixing with smaller gauge needle. A more vigorous mixing is expected from a stronger collision impact of impinging jet streams of the components A and B against each other. It was contrary to our expectation that the flow distance was longer as the delivery speed was faster. However, this result may be explained by the fact that slow delivery of the glue allows a longer time for progressive solidification to occur starting from the first part of mixed components to the last part.

TABLE 4

Clotting Rate Depending on Delivery Speed of Fibrin Glue by Using Impinging Dual Syringe Device of 22Ga or 25Ga Size.

| Size of Device | Clotting Rate by Flow Distance, cm Delivery Speed, second/ml | | | |
|---|---|---|---|---|
| | 2 | 4 | 6 | 9 |
| 22Ga | 5.8 | 3.5 | 2.0 | 1.5 |
| 25Ga | 4.5 | 2.7 | 1.6 | 1.3 |

A slow setting of fibrin glue due to a slow diffusion-limited coagulation was observed from the color visualization experiment, in which color streaks smeared only slightly even after an hour. It would not be surprising that the mechanical strength would continue to develop over many hours after initial setting of the fibrin glue because the coagulation reaction will be phased into a mass transfer limited process and even more slower as the solidified networks become thicker.

As expected, the clotting rate was slowest (long flow distance) when dual syringe having adjoined needles device was used. In this device two components are mixed only at the exiting point of the tips. A better mixing is achieved with the single tube endoscopic delivery device than the dual syringe device, probably because of generation of eddy flow in the cell at the end point of Y-shaped lumens where components A and B are met. Any additional mixing during passage through the endoscopic tube is anticipated to be minimal since the flow in the tube is expected to be a laminar flow as dictated by the low Reynolds number calculated under a normal application condition.

The mixing in this type of device is improved when the delivery speed is increased as a result of increased Reynolds number. However, the bubbles tend to be generated. This is probably due to the high-speed cavitations effect during passage through the irregular spaces in the device. Bubble inclusions set in the mass of coagulated fibrin glue is not desirable. Also frequent clogging inside of the device when delivery of the fibrin glue is momentarily stopped is another disadvantage in this type of device.

When using the impinging dual syringe application device, the mixing is more efficient probably due to the impact force of ejecting jet streams of component A and component B. This would allow a vigorous and intimate mixing of two liquids free of drag effect. The impinging impact force is proportional to the mass flow rate and therefore the effect of the tube size on mixing efficiency will be minimal. Therefore, fibrin glue of a larger volume can be delivered by using tubes of larger size without impairing the mixing effect.

In this disclosure, there is shown and described only the preferred examples of the invention, but, as aforementioned, it is to be understood that the invention is capable of use in various other combinations and environments and is capable of changes or modifications within the scope of the inventive concepts as expressed herein.

What is claimed is:

1. A delivery device to apply two-component adhesives to a treatment site, the delivery system comprising:
   a pair of syringe bodies to store a first and a second adhesive components, respectively;
   a pair of plungers associated with the syringe bodies to expel the first and the second component from the syringe bodies; and
   a pair of needles connected to the syringe bodies to provide separate passages for the components, wherein the pair of needles have distal end surfaces which are separated from each other by a predetermined distance, and face each other by an angle in the range of 10° to less than 180°.

2. The delivery device to apply two-component adhesives according to claim 1, wherein the needles includes needle bodies which are is connected to the syringe bodies and bent to be held together, and needle ends which extend from the needle bodies, and bent to separate the distal end surfaces.

3. The delivery device to apply two-component adhesives according to claim 2, wherein the needle ends are bent to have the shape of a partially opened circle which has an open portion on the symmetry axis of the needle bodies.

4. The delivery device to apply two-component adhesives according to claim 1, wherein the distal end surfaces face each other with an angle in the range of 30° to less than 120°.

5. The delivery device to apply two-component adhesives according to claim 1, further comprising a syringe holder to receive and secure the syringe bodies in parallel.

6. The delivery device to apply two-component adhesives according to claim 1, further comprising a connecting member which connects the ends of the plungers to actuate the plungers simultaneously.

7. A delivery device to apply two-component adhesives to a treatment site, the delivery system comprising:
   a pair of syringe bodies to store a first and a second adhesive components, respectively;
   a pair of plungers associated with the syringe bodies to expel the first and the second component from the syringe bodies; and
   a pair of needles connected to the syringe bodies to provide separate passages for the components, wherein the needles includes needle bodies which are connected to the syringes and bent to be held together, and needle ends which extends from the needle bodies, and bent outwardly and then inwardly along with the direction of ejected components to separate the distal end surfaces of the needle ends.

8. A delivery device comprising:
   a syringe body to separately store at least two adhesive components; and
   at least two needles connected to said syringe body, each needle used to expel one of said adhesive components, wherein said needles have distal end surfaces that are separated from each other and face each other by an angle in the range of 10° to less than 180°.

* * * * *